(12) United States Patent
Yoon et al.

(10) Patent No.: US 10,226,060 B2
(45) Date of Patent: Mar. 12, 2019

(54) LACTOCOCCUS GARVIEAE BACTERIOPHAGE LAC-GAP-1 AND USE THEREOF IN SUPPRESSING PROLIFERATION OF LACTOCOCCUS GARVIEAE BACTERIA

(71) Applicant: Intron Biotechnology, Inc., Gyeonggi-do (KR)

(72) Inventors: Seong Jun Yoon, Seoul (KR); Sang Hyeon Kang, Seoul (KR); Soo Youn Jun, Seoul (KR); An Sung Kwon, Gyeonggi-do (KR); Soon Hye Hwang, Seoul (KR)

(73) Assignee: INTRON BIOTECHNOLOGY, INC., Gyeonggi-Do (KR)

(\*) Notice: Subject to any disclaimer, the term of this patent is extended or adjusted under 35 U.S.C. 154(b) by 0 days.

(21) Appl. No.: 15/543,618

(22) PCT Filed: Jan. 5, 2016

(86) PCT No.: PCT/KR2016/000028
§ 371 (c)(1),
(2) Date: Jul. 14, 2017

(87) PCT Pub. No.: WO2016/114517
PCT Pub. Date: Jul. 21, 2016

(65) Prior Publication Data
US 2018/0000125 A1    Jan. 4, 2018

(30) Foreign Application Priority Data
Jan. 16, 2015 (KR) .................. 10-2015-0008012

(51) Int. Cl.
| | |
|---|---|
| *A61K 39/02* | (2006.01) |
| *A61K 39/00* | (2006.01) |
| *A61K 49/00* | (2006.01) |
| *A23K 20/195* | (2016.01) |
| *A61K 35/76* | (2015.01) |
| *C12N 7/00* | (2006.01) |
| *A23K 10/16* | (2016.01) |
| *A23K 10/18* | (2016.01) |
| *A23K 50/80* | (2016.01) |

(52) U.S. Cl.
CPC ............. *A23K 20/195* (2016.05); *A23K 10/16* (2016.05); *A23K 10/18* (2016.05); *A23K 50/80* (2016.05); *A61K 35/76* (2013.01); *C12N 7/00* (2013.01); *C12N 2795/10121* (2013.01); *C12N 2795/10122* (2013.01); *C12N 2795/10132* (2013.01)

(58) Field of Classification Search
CPC ......... A61K 39/00; A61K 39/02; A61K 39/09
USPC ................ 424/9.1, 9.2, 184.1, 185.1, 234.31
See application file for complete search history.

(56) References Cited

FOREIGN PATENT DOCUMENTS

| JP | 5649256 B1 | 1/2015 |
|---|---|---|
| KR | 10-2000-0021520 A | 1/2001 |
| WO | WO-2016/114517 A1 | 7/2016 |

OTHER PUBLICATIONS

Dictionary of Microbiology and Molecular Biology, second edition, Singleton and Sainsbury, eds., John Wiley & Sons, New York, NY, p. 452, 1993.*
Nakai, T. et al. (1999) Protective Effects of Bacteriophage on Experimental *Lactococcus garvieae* Infection in Yellowtail. Diseases of Aquatic Organisms. 37(1):33-41.
NCBI, Lactococcus lactis subsp. lactis Strain S0, complete genome. GenBank accession No. CP010050.1 (Dec. 23, 2014).
International Search Report dated Apr. 25, 2016 by the International Searching Authority for International Patent Application No. PCT/KR2016/000028, which was filed on Jan. 5, 2016 and published as WO 2016/114517 on Jul. 21, 2016 (Inventor—Yoon et al.; Applicant—Intron Biotechnology, Inc.) (Original—4 pages/Translation—2 pages).

\* cited by examiner

*Primary Examiner* — Rodney P Swartz
(74) *Attorney, Agent, or Firm* — Ballard Spahr LLP

(57) ABSTRACT

The present invention relates to a Myoviridae bacteriophage Lac-GAP-1 that is isolated from the nature and can kill specifically *Lactococcus garvieae* cells, which has a genome represented by the nucleotide sequence of SEQ ID NO: 1 (Accession NO: KCTC 12686BP), and a method for preventing and treating the infections of *Lactococcus garvieae* using the composition comprising said bacteriophage as an active ingredient.

2 Claims, 2 Drawing Sheets
Specification includes a Sequence Listing.

LACTOCOCCUS GARVIEAE BACTERIOPHAGE LAC-GAP-1 AND USE THEREOF IN SUPPRESSING PROLIFERATION OF LACTOCOCCUS GARVIEAE BACTERIA

CROSS-REFERENCE TO RELATED APPLICATIONS

This application is a U.S. National Phase Application of International Application No. PCT/KR2016/000028, filed Jan. 5, 2016, which claims priority to Korean Application No. 10-2015-0008012, filed Jan. 16, 2015, each of which are hereby incorporated by reference in their entirety.

REFERENCE TO SEQUENCE LISTING

The Sequence Listing submitted Jul. 13, 2017, as a text file named "08162_0034U1_Sequence_Listing.txt," created on Jun. 16, 2017, and having a size of 44,233 bytes is hereby incorporated by reference pursuant to 37 C.F.R. § 1.52(e)(5).

BACKGROUND OF THE INVENTION

1. Field of the Invention

The present invention relates to a bacteriophage isolated from the nature that infects and kills *Lactococcus garvieae* cells, and a method for preventing and treating the infections of *Lactococcus garvieae* using a composition comprising the bacteriophage as an active ingredient. More particularly, the present invention relates to a Myoviridae bacteriophage Lac-GAP-1 that is isolated from the nature and can kill *Lactococcus garvieae* cells specifically, which has a genome represented by the nucleotide sequence of SEQ. ID. NO: 1 (Accession NO: KCTC 12686BP), and a method for preventing the infections of *Lactococcus garvieae* and thereafter treating them using the composition comprising said bacteriophage as an active ingredient.

2. Description of the Related Art

*Lactococcus garvieae* is a Gram-positive ovoid coccus and has two kinds of serotypes according to the presence of capsular antigen (K). *Lactococcus garvieae* is also known as a pathogenic bacterium causing lactococcosis especially in aquatic species and sometimes gives rise to endocarditis and mastitis in several animals including cow, buffalo, pig and fowl.

When being infected with *Lactococcus garvieae*, fish is suffered from lactococcosis to rotate in water and show darkened body color, exophthalmos, bleeding of bronchial caps, basal hemorrhage and abdominal distention. In terms of anatomical signs, the fish manifests discoloration of liver, enlargement of digestive tract, and bleeding of internal organs, and further reveals hemic ascites and abdominal hemorrhage. Outbreak of lactococcosis can be influenced by several factors including deterioration of environmental conditions, inappropriate farming methods, and inappropriate feeds. Moreover, lactococcosis is commonly frequent in adult fish rather than in juvenile fish, so that the resulting economical damage could be relatively bigger, compared to other bacterial diseases. Therefore, it is necessary to watch carefully the state of fish in aquafarms and inspect their abnormal behaviors, especially at a dangerous period when water becomes warmer.

The fish aquaculture industry continues to develop rapidly every year, because it makes food resources acquired easily when insufficient in the wild fish capture. However, as the aquaculture industry develops increasingly, environmental pollution caused by feeds increases around aquafarms. Particularly, a lot of antibiotics included in the feeds are spread widely to rather threaten human health. In the fish aquaculture industry, the antibiotics have been utilized mostly to prevent bacterial infections due to hygienic problems. But, it is pointed out that such universal use of antibiotics without any restraint should be the most important issue. In practice, pathogens become resistant to the antibiotics due to such abuse in aquafarms. As a consequence, new antibiotic-resistant bacterial strains are emerging increasingly and brings about the change of bacterial flora, leading to severe situations.

In Korea, the use of antibiotics to prepare feed additives has been prohibited across the board in July, 2011. Nevertheless, a lot of aquafarms still utilize the antibiotics prescribed in the field, because of the increased incidence, the reduction of productive yields and the like. Therefore, it is urgently requested to develop a novel method for preventing the bacterial infections and thereafter treating them effectively. In order to control the disease outbreak among farming fish, vaccines also have been developed. However, the variety of vaccines cannot catch up with the variety of diseases. In addition, to overcome the multiple diseases broken at the same time, a combined control method to treat them along with the vaccines is required.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that Micrococcus colonies melted and became transparent by something unknown. In 1917, a French bacteriologist d'Herelle found out that *Shigella dysenteriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella Typhi*, and *Vibrio cholerae* have been continuously identified.

Owing to the unique capability of bacteriophage to kill bacteria, bacteriophages have been studied and anticipated as a better method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

Furthermore, the recent regulation of using antibiotics is fortified by the government world-widely. The interest on bacteriophages is increasing more and also industrial applications are increasily achieved.

Therefore, the present inventors tried to develop a composition applicable for the prevention or treatment of *Lactococcus garvieae* infections by using a bacteriophage that is isolated from the nature and can kill *Lactococcus garvieae* cells selectively, and further to establish a method for preventing or treating the infections of *Lactococcus garvieae* using the composition. As a result, the present inventors isolated bacteriophages suitable for this purpose and secured the nucleotide sequence of the genome that distinguishes the bacteriophage of the present invention from other bacteriophages. Then, we have developed a composition comprising the isolated bacteriophage as an active ingredient, and confirmed that this composition could be efficiently used to prevent and treat the infections of *Lactococcus garvieae* infections, leading to the completion of the present invention.

SUMMARY OF THE INVENTION

It is an object of the present invention to provide a Myoviridae bacteriophage Lac-GAP-1 that is isolated from the nature and can kill *Lactococcus garvieae* cells specifically, which has the genome represented by the nucleotide sequence of SEQ. ID. NO: 1 (Accession NO: KCTC 12686BP).

It is another object of the present invention to provide a composition applicable for the prevention of *Lactococcus garvieae* infections, which comprises the bacteriophage Lac-GAP-1 that can infect and kill *Lactococcus garvieae* cells, as an active ingredient and a method for preventing the infections of *Lactococcus garvieae* using said composition.

It is another object of the present invention to provide a composition applicable for the treatment of *Lactococcus garvieae* infections, which comprises the bacteriophage Lac-GAP-1 that can infect and kill *Lactococcus garvieae* cells, as an active ingredient and a method for treating the infections of *Lactococcus garvieae* using said composition.

It is another object of the present invention to provide an immersion agent (medicine bath agent) for preventing and treating the infections of *Lactococcus garvieae* using said composition.

It is also an object of the present invention to provide a feed additive effective upon farming by preventing and treating the infections of *Lactococcus garvieae* using said composition.

To achieve the above objects, the present invention provides a Myoviridae bacteriophage Lac-GAP-1 that is isolated from the nature and can kill specifically *Lactococcus garvieae* cells, which has the genome represented by the nucleotide sequence of SEQ. ID. NO: 1 (Accession NO: KCTC 12686BP), and a method for preventing and treating the infections of *Lactococcus garvieae* using a composition comprising the bacteriophage as an active ingredient.

The bacteriophage Lac-GAP-1 has been isolated by the present inventors and then deposited at Korean Collection for Type Cultures, Korea Research Institute of Bioscience and Biotechnology in Oct. 1, 2014 (Accession NO: KCTC 12686BP). In addition, the present invention also provides an immersion agent and a feed additive applicable for the prevention or treatment of *Lactococcus garvieae* infections, which comprises the bacteriophage Lac-GAP-1 as an active ingredient.

Since the bacteriophage Lac-GAP-1 included in the composition of the present invention kills *Lactococcus garvieae* cells efficiently, it is regarded as effective to prevent or treat lactococcosis (infections) caused by *Lactococcus garvieae*. Therefore, the composition of the present invention can be utilized for the prevention and treatment of lactococcosis caused by *Lactococcus garvieae*.

In this description, the term "treatment" or "treat" indicates (i) to suppress the lactococcosis caused by *Lactococcus garvieae*; and (ii) to relieve the lactococcosis caused by *Lactococcus garvieae*.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The pharmaceutically acceptable carrier included in the composition of the present invention is the one that is generally used for the preparation of a pharmaceutical formulation, which is exemplified by lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage Lac-GAP-1 is included as an active ingredient. At this time, the bacteriophage Lac-GAP-1 is included at the concentration of $1 \times 10^1$ pfu/ml~$1 \times 10^{30}$ pfu/ml or $1 \times 10^1$ pfu/g~$1 \times 10^{30}$ pfu/g, and preferably at the concentration of $1 \times 10^4$ pfu/ml~$1 \times 10^{15}$ pfu/ml or $1 \times 10^4$ pfu/g~$1 \times 10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as an immersion agent or a feed additive according to the purpose of use, but not always limited thereto.

Advantageous Effect

The method for preventing and treating the infections of *Lactococcus garvieae* using this composition comprising the bacteriophage Lac-GAP-1 as an active ingredient, has the advantage of high specificity for *Lactococcus garvieae*, compared with the conventional methods based on the chemical materials including the conventional antibiotics. That means, the composition of the present invention can be used for preventing or treating the infections of *Lactococcus garvieae* specifically without affecting normal microflora, and accordingly has fewer side effects. In general, when chemical materials such as antibiotics are used, commensal bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
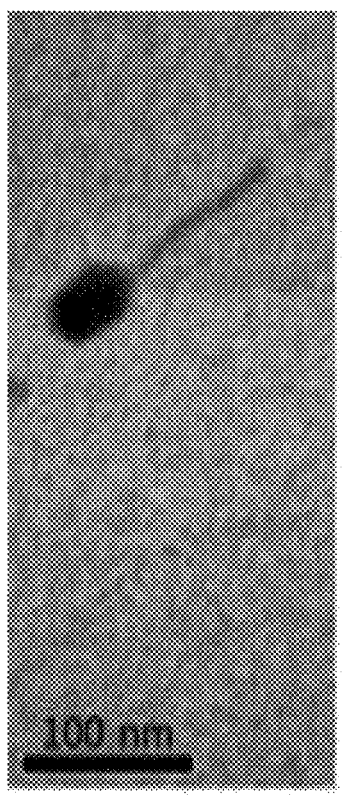
FIG. 1 is an electron micrograph showing the morphology of the bacteriophage Lac-GAP-1.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation of Bacteriophage Capable of Killing *Lactococcus garvieae*

Samples were collected from the nature to screen the bacteriophage capable of killing *Lactococcus garvieae*. In the meantime, the *Lactococcus garvieae* cells used for the bacteriophage isolation herein were obtained from Korean Collection for Type Cultures, Korea Research Institute of Bioscience and Biotechnology (Accession NO: KCTC 5619).

The isolation procedure of the bacteriophage is described in detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with *Lactococcus garvieae* at the ratio of 1/1000, followed by shaking culture at 30-C for 3~4 hours. Upon completion of the culture, centrifugation was performed at 8,000 rpm for 20 minutes and supernatant was recovered. The recovered supernatant was inoculated with *Lactococcus garvieae* at the ratio of 1/1000, followed by shaking culture at 30° C. for 3~4 hours. When the sample contained the bacteriophage, the above procedure was repeated total 5 times in order to increase the titer of the bacteriophage. After repeating the procedure 5 times, the culture solution proceeded to centrifugation at 8,000 rpm for minutes and the resulting supernatant was recovered. The recovered supernatant was filtrated by using a 0.45 μm filter. The obtained filtrate was used in spot assay for examining whether or not the bacteriophage capable of killing *Lactococcus garvieae* was included therein.

Spot assay was performed as follows; TSB medium was inoculated with *Lactococcus garvieae* at the ratio of 1/1000, followed by shaking culture at 30° C. for overnight. 3 ml (1.5 of $OD_{600}$) of the culture broth of *Lactococcus garvieae* prepared above was spread on the TSA (Tryptic Soy Agar; pancreatic digest of casein, 15 g/L; papaic digest of soybean, 5 g/L; sodium chloride, 5 g/L; agar, 15 g/L) plate. The plate stood in a chamber for about 30 minutes to dry. After drying, 10 μl of the resulting filtrate was spotted directly onto the surface of the *Lactococcus garvieae* lawns and dried for about 30 minutes. Following drying, the plate was incubated at 30° C. for a day and then, examined for the formation of clear zone on the surface of the bacterial lawns. If a clear zone was generated where the filtrate was dropped, it could be judged that the bacteriophage capable of killing *Lactococcus garvieae* was included in the filtrate. Through the above procedure, the filtrate containing the bacteriophage having the killing ability of *Lactococcus garvieae* could be obtained.

After that, the bacteriophage was isolated from the filtrate confirmed above to have the bacteriophage capable of killing *Lactococcus garvieae*. The conventional plaque assay was used for the isolation of pure bacteriophages. In detail, a plaque formed in the course of the plaque assay was picked up by using a sterilized tip, which was then added to the culture solution of *Lactococcus garvieae*, followed by culturing at 30° C. for 4~5 hours. Upon completion of the culture, centrifugation was performed at 8,000 rpm for 20 minutes to obtain supernatant. The recovered supernatant was inoculated with *Lactococcus garvieae* culture at the ratio of 1/50, followed by culturing at 30° C. for 4~5 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated by using the plague formed above. After at least 5 times of repeated procedure, the solution containing the pure bacteriophage was obtained. The procedure for the isolation of the pure bacteriophage was generally repeated until the generated plaques became similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated above was identified as belonging to the family Myoviridae.

The solution containing the pure bacteriophage confirmed above proceeded to purification. The culture broth of *Lactococcus garvieae* was added to the solution containing the pure bacteriophage at the volume of 1/50 of the total volume of the bacteriophage solution, followed by culturing again for 4~5 hours. Upon completion of the culture, centrifugation was performed at 8,000 rpm for 20 minutes to obtain supernatant. This procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 Mk of the filtrate until reaching 10% PEG 8000/0.5 M NaCl, which stood at 4° C. for 2~3 hours. Then, centrifugation was performed at 8,000 rpm for 30 minutes to obtain the bacteriophage precipitate. The resulting bacteriophage precipitate was resuspended in 5 ml of buffer (10 mM Tris-HCl, 10 mM $MgSO_4$, 0.1% Gelatin, pH 8.0). This solution was called as the bacteriophage suspension or bacteriophage solution.

As a result, the pure bacteriophage purified above was collected, which was named as the bacteriophage Lac-GAP-1 and then deposited at Korean Collection for Type Cultures, Korea Research Institute of Bioscience and Biotechnology in Oct. 1, 2014 (Accession NO: KCTC 12686BP).

Example 2: Separation and Sequence Analysis of the Bacteriophage Lac-GAP-1 Genome The genome of the bacteriophage Lac-GAP-1 was separated as follows. The genome was separated from the bacteriophage suspension obtained in Example 1. First, in order to eliminate DNA and RNA of *Lactococcus garvieae* included in the suspension, DNase I and RNase A were added 200 U each to 10 ml of the bacteriophage suspension, which was incubated at 37° C. for 30 minutes. 30 minutes later, to remove the DNase I and RNase A activity, 500 μl of 0.5 μM ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. After that, 500 μl of 10% sodium dodecyl sulfate (SDS) solution was added thereto, followed by incubation at 65° C. for 1 hour. 10 ml of the mixture of phenol:chloroform:isoamylalcohol in a ratio of 25:24:1 was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the bacteriophage Lac-GAP-1 genome.

The nucleotide sequence of the genome of the bacteriophage Lac-GAP-1 obtained above was analyzed by Next Generation Sequencing (NGS) using illumina Mi-Seq device at National Instrumentation Center for Environmental Management, Seoul National University. As a result, it is suggested that the final genome of bacteriophage Lac-GAP-1 have 34,587 bp of size and the nucleotide sequence of the whole genome has SEQ. ID. NO: 1.

Similarity of the genomic sequence of the bacteriophage Lac-GAP-1 obtained above with the previously reported bacteriophage genome sequences was investigated by using BLAST. From the BLAST result, it was difficult to find bacteriophage sequences having more than 50% of sequence homology with this bacteriophage sequence.

Based upon this result, it is concluded that the bacteriophage Lac-GAP-1 should be a novel bacteriophage not reported previously.

Example 3: Investigation of Killing Ability of the Bacteriophage Lac-GAP-1 Against *Lactococcus garvieae*

Figure 2:
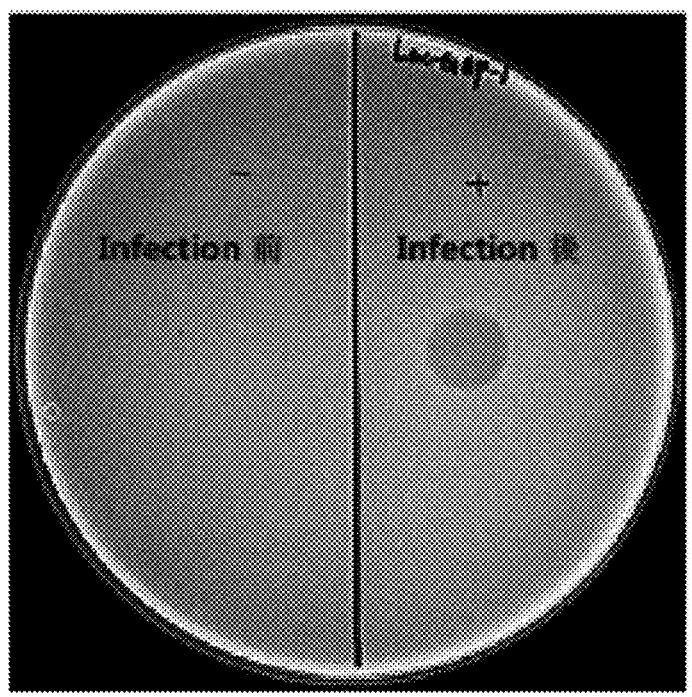
FIG. 2 is a photograph illustrating the capability of the bacteriophage Lac-GAP-1 to kill *Lactococcus garvieae* cells. The clear zone on the dish is the formation of plaque by lysis of bacteria cells.

The killing ability of the isolated bacteriophage Lac-GAP-1 against *Lactococcus garvieae* was investigated. To do so, the formation of clear zone was observed by the spot assay by the same manner as described in Example 1. The *Lactococcus garvieae* used for this investigation were total 9 strains which had been isolated and identified as *Lactococcus garvieae* previously by the present inventors. The bacteriophage Lac-GAP-1 demonstrated the killing ability against 7 strains of *Lactococcus garvieae* used in this experiment. The representative result of the killing ability test is shown in FIG. 2. In the meantime, the activity of the bacteriophage Lac-GAP-1 to kill *Edwardsiella tarda*, *Vibrio anguillarum*, *Vibrio ichthyoenteri*, *Streptococcus parauberis* and *Streptococcus iniae* was also investigated. As a result, it is decided that the bacteriophage Lac-GAP-1 did not have the killing activity against these microorganisms.

Therefore, it is confirmed that the bacteriophage Lac-GAP-1 has the specific ability to kill *Lactococcus garvieae* cells and a broad antibacterial spectrum against *Lactococcus garvieae*, suggesting that the bacteriophage Lac-GAP-1 of the present invention could be used as an active ingredient of the composition for preventing and treating the infections of *Lactococcus garvieae*.

Example 4: Preventive Effect of Bacteriophage Lac-GAP-1 on the Infections of *Lactococcus garvieae*

100 μl of the bacteriophage Lac-GAP-1 solution at $1 \times 10^8$ pfu/mL was added to a tube containing 9 mL of TSB. To another tube containing 9 mL of TSB, the same amount of TSB was further added. *Lactococcus garvieae* culture solution was added to each tube until $OD_{600}$ reached 0.5. Then, the tubes were transferred in a 30° C. incubator, followed by shaking-culture, during which the growth of *Lactococcus garvieae* was observed. As presented in Table 1, the growth of *Lactococcus garvieae* was inhibited in the tube adding the bacteriophage Lac-GAP-1 solution, while the growth of *Lactococcus garvieae* was not inhibited in the tube not adding the bacteriophage solution.

TABLE 1

Inhibition of growth of *Lactococcus garvieae*

| Treatment | $OD_{600}$ | | |
| --- | --- | --- | --- |
| | 0 min. | 60 min. | 120 min. |
| −bacteriophage solution | 0.50 | 1.01 | 1.60 |
| +bacteriophage solution | 0.50 | 0.38 | 0.21 |

The above results indicate that the bacteriophage Lac-GAP-1 not only inhibited the growth of *Lactococcus garvieae* but also could kill the bacterial cells. Therefore, the bacteriophage Lac-GAP-1 can be used as an active ingredient of the composition in order to prevent the infections of *Lactococcus garvieae*.

Example 5: Therapeutic Effect of Bacteriophage Lac-GAP-1 on the Infections of *Lactococcus garvieae*

Therapeutic effect of the bacteriophage Lac-GAP-1 on the flatfish suffered from lactococcosis by the infections of *Lactococcus garvieae* was investigated. Particularly, total 2 groups of juvenile flatfish (10 juvenile flatfish per group, body length 6-9 cm) at 4 months old were prepared, which were cultured separately in different water tanks for 14 days. Surrounding environment of the water tanks was controlled. The temperature and humidity in the laboratory where the water tanks stayed were also controlled. From the 5$^{th}$ day of the experiment, feeds adding *Lactococcus garvieae* cells at $1\times10^8$ CFU/g were provided twice a day for 3 days according to the conventional feed supply procedure. Flatfish subjects showing clinical symptoms of lactococcosis from the last day of this procedure, were observed in both water tanks. From the next day of providing feeds adding *Lactococcus garvieae* cells for 3 days (the $8^{th}$ day of the experiment), flatfish of the experimental groups (adding the bacteriophage) were fed with feeds adding the bacteriophage Lac-GAP-1 at $1\times10^8$ PFU/g according to the conventional feed supply procedure, while flatfish of the control group (without the bacteriophage) were fed with the same feeds without the bacteriophage Lac-GAP-1 according to the conventional procedure. After the $8^{th}$ day of the experiment, all the test animals were examined whether being suffered from lactococcosis or not. The outbreak of lactococcosis was detected by measuring body darkening index. The measurement of body darkening index was performed by the conventional method obtaining Dark Coloration (DC) score (0: normal, 1: light coloration, 2: dark coloration). The results are shown in Table 2.

TABLE 2

Dark coloration score (average values)

| | Days | | | | | | |
|---|---|---|---|---|---|---|---|
| | D8 | D9 | D10 | D11 | D12 | D13 | D14 |
| Control group (−bacteriophage) | 1.0 | 1.3 | 1.4 | 1.5 | 1.3 | 1.2 | 1.2 |
| Experimental group (+bacteriophage) | 1.0 | 0.7 | 0.3 | 0.2 | 0.2 | 0.1 | 0 |

From the above results, it is confirmed that the bacteriophage Lac-GAP-1 of the present invention could be very efficient to treat the infections of *Lactococcus garvieae*.

Example 6: Preparation of Feed Additives and Feeds

Feed additives were prepared by adding the bacteriophage Lac-GAP-1 solution at the concentration of $1\times10^8$ pfu/g feed additives. The preparation method thereof was as follows: Maltodextrin (40%, w/v) was added to the bacteriophage solution and then trehalose was added to reach 10 weight %. After mixing well, the resulting mixture was freeze-dried. Lastly, the dried mixture was grinded into fine powders. The drying procedure above can be replaced with drying under a reduced pressure, drying at warm temperature, or drying at room temperature. To prepare the control for comparison, feed additives that did not contain the bacteriophage but contained only buffer (10 mM Tris-HCl, 10 mM $MgSO_4$, 0.1% Gelatin, pH 8.0) were prepared.

The above two kinds of feed additives were mixed with raw fish-based moist pellet at the volume of 250 times the volume of additives, resulting in two kinds of final feed additives.

Example 7: Preparation of an Immersion Agent (Medicine Bath Agent)

An immersion agent comprising $1\times10^8$ pfu/ml of bacteriophage Lac-GAP-1 was prepared. The preparation method was as follows: $1\times10^8$ pfu of the bacteriophage Lac-GAP-1 was added to 1 mL of buffer, which was well mixed. To prepare the control, the buffer itself that is the same with the one used for the mixture of the bacteriophage solution was prepared.

The prepared two kinds of immersion agents were diluted with water at the ratio of 1:1,000, resulting in the final immersion agents for the experiment.

Example 8: Effect on Flatfish Aquafarming

The effect of the feeds and the immersion agents prepared in Example 6 and Example 7 on flatfish aquafarming was investigated. Particularly, the investigation was focused on the mortality. Total 400 flatfish were grouped into two, 200 flatfish for each group, which proceeded to the following experiment (group A; fed with feeds, group B; treated with immersion agent). Each group was divided to two sub-groups again, group of 100 flatfish each (sub-group-①: treated with the bacteriophage Lac-GAP-1, sub-group-②: not-treated with the bacteriophage Lac-GAP-1). The flatfish used for this experiment were the juvenile flatfish at 4 months old. Each sub-group flatfish were aquacultured in separate water tanks placed at a certain space interval. Each sub-group was distinguished and named as shown in Table 3.

TABLE 3

Sub-groups of aquafarming experiment of flatfish

| | Sub-group | |
|---|---|---|
| Treatment | Treated with the bacteriophage Lac-GAP-1 | Not-treated with the bacteriophage |
| Fed with feeds | A-① | A-② |
| Treated with immersion agents | B-① | B-② |

Feeds were provided according to the conventional feed supply procedure as presented in Table 3 with the feeds prepared as described in Example 6. The treatment of immersion agent was also performed by the conventional procedure as presented in Table 3 with the immersion agent prepared as described in Example 7. The test result is shown in Table 4.

TABLE 4

Mortality of flatfish in aquafarming

| Group | Mortality (%) |
|---|---|
| A-① | 5 |
| A-② | 22 |
| B-① | 9 |
| B-② | 24 |

The above results indicate that the feeds prepared by the present invention and the immersion agent prepared according to the present invention are effective to reduce the mortality of the cultured flatfish. Therefore, it is concluded that the composition of the present invention could be efficiently applied to improve outcomes of flatfish aquaculture.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating infections of *Lactococcus garvieae*, the method comprising a step of administering to a subject a composition comprising Myoviridae bacteriophage Lac-GAP-1 (Accession NO: KCTC 12686BP) that is isolated from nature and can kill *Lactococcus garvieae* cells specifically, which has the genome represented by the nucleotide sequence of SEQ ID NO: 1, as an active ingredient.

2. The method according to claim 1, wherein said composition is administered to the subject in the form of an immersion agent or a feed additive.

* * * * *

SEQUENCE LISTING

<160> NUMBER OF SEQ ID NOS: 1

<210> SEQ ID NO 1
<211> LENGTH: 34587
<212> TYPE: DNA
<213> ORGANISM: Bacteriophage Lac-GAP-1

<400> SEQUENCE: 1

```
gaaagccaaa gggactaggt tacctgtgat agactggtta ggcgtgaagt acggagtaac    60
ccagagggag ggggatatgc ccccatagtt tctctcctaa gctctttaaa ttattttaa    120
taatatttat cataaataat ttaagataca taagaagacc aatcacggct ctgtggcaaa    180
ttacgattac ctaataccttt tggttcttct tgcttcacat tgaatagctt gtcagacttc    240
tgacggttgc aagtccagtg agcaagctgt aagttatcca tcgctgaagg atgaccacct    300
ttgttaattg gaatgatgtg gtcaacaact ggactcaatg gatcaggagc tttcaatctc    360
ttatcgattg gcttgccaca tattccacaa gtgttctgtg tctttaaaag aatctttcta    420
ttcttatcaa aggctacacg atgcgcacca gtacggtcag cacgtaatgc tatgggaggt    480
cacctcactt tctccacaca aaaagccaac agaatatatc cgctggcttt atttgtttta    540
tttgatgata ctataataca acatttatct tgtcagtttt cgcccaaaag gtgacaaatt    600
accagaagcc gtcacatatc tcatcatact tctcaagtat tgctcttctc tttctaaagt    660
attggcgctc agttatgtga cacttatcag ctatctctgg tactgtataa cgtttaccag    720
ataaccaacg gtagtggaat accaattgca tatcttcatc ctctccaaac caatcttgta    780
actcattgat tcggttctta aactcatata gactttggag tttactgtca gcatcccatt    840
tcataaccat atcttctact ggctttgaga ttatacttga cctaccacca cctacattat    900
tatcatgtga ttgtttaact tctaactcat acttgcgata ttgaatagcg tggtcaattc    960
gttgacacat aaagagcttc ttctctatag cttttcaagtc gctgtcagta aggttatatc   1020
ttctactcat agtgtcttaa ctccttatat ttatgatata atagtagtta agaaatctgt   1080
ttttaaagcc cattgcagtg ggctttttt ggtactcaag aaaattagtc attgaatact   1140
gtgctatagt gctataatat atttgagtta ataaatttaa ctacatcatt agaaaggaga   1200
attatatgtc taaaacagat aaagaattga cttcagaaat tgtaattgct tatttaggta   1260
atcataatta cgcttatagc aatgatgaaa ttactagctt gattaaagat gttcatgaaa   1320
ctttgcgtgc attagattaa ataattaatt tcgaagttca ccaattagct cactaatggc   1380
taccatttct gagctttta ttttatttt atctctttct ttaattagta aatatataat   1440
ataatcggaa agtgtcttta tatttgttaa cctctatcac taaatgtttg acaggtattt   1500
ttttattttt attaaaacac tcgtttttta ctcatctatt cttctaaaat acaagatatt   1560
catcacgttt aaagaaatca tttcaccagt ttcactatct ttgacatgaa accatttttt   1620
tccaaaactt ataacctcag ctaaattatc ttccgttgca acgaatttaa tgctatatcc   1680
tttgaatatt gctaaatagg tatgtttttt cattccacaa cctcctcgat ataggcaact   1740
ttgaaagctg cgttgttagc agtgtgccaa cctgagttgt tatcagtgca ccaacctgcg   1800
ttgctttcga tatactcaat aacatcagcg aaactaccag cttcaacaaa ctgttgtctt   1860
gaacgaatta ctccgtcttg gtccataaac gagctactta ctaatctaaa ttttttcatc   1920
tccacctcaa tccatatgtt tatgaagcca tttcatgata tagccaccta tcattccacc   1980
```

```
aataaagccc agtataatgt aactcatcat tcctccccga acacgttctc agactcgtca    2040
aggtctgagc ggttgatttc tcttgcgtac caccaccact tacccatct tttacaaaat    2100 atatctttat gaactgcttc aggcttatgc ccgaacagct tacacattag tttcattggt    2160
tgtcctcatt ttcgttaatt gttttagagc attgtagaaa gcatccacta tttttctaac    2220
agtttcacta actctaattc ctaattcagc aacgttctta aatccatatt ttctgacaaa    2280
attatttcgc catcttagaa gcttaatttg ccgttttta gttgcttgtc tttgcttctt    2340
ccagcttgat ttcatttgac tacctcacct ttccaaacat aactattact ccgcagagca    2400
aaatcacagc tcctataatc attatccaaa aagctgggta aataaagctt gctgctcctg    2460
caattgtgaa tatttttccaa agtaataatg ttgctatcca tacccagaat gatacaacca    2520
taacagtacc tccgagccat gctactatta ctgcaataaa ttcttttatc attttttatt    2580
tctccttgta atcactgcct ttataaggct tttttatt tggttaaaac gggctatatc    2640
caaaatgggt tatatccaat taacggtgat tggaagtcgt catcaatgtc atccccatcg    2700
aattctaact ctctaaattc atcatccaat tggtcatagt cacgtgctaa tttatcatac    2760
tcgtgttcag cttcaatgag attagatttt aagacaacta cgtgtgctgt aagcaatcgg    2820
atttcatgat tcttacgttc gagaactttc tgaacttctt caatggtcat agatctaaca    2880
ctattactca cctgtaacct ccacaaatgg tcttgttaga ggattaagat atgctgtcat    2940
caactgattg ctttctgagt catatatcca ctttgttaat ccattttctt caatccaaaa    3000
ttcttcttct tcaaagcttt caaactctcg ctcatcatat ttttcaaaaa tttccgcaat    3060
cttcttcggt atgctgagtt tgggctggtt tgcaaactct actttcttga ttagtggctc    3120
ttctaaatca tagaatttcc cccagtcctt cttgttacct gttttccg cttttttcaaa    3180 agcaaagcag actttctcta cttcttgtcg tgctgtgtct ttactcatct ttactcctcc    3240
accaattcat ctaccgagca gccgagggct tgggcaacta cttgtaccat aagacccgta    3300
ccgtcagaat ttgatcctgc tccatctgct tctatacttg ctaaagtcat ggccataatt    3360
cctgctttaa aagatggttc aatctcattc accttttttg ctagctcaat tacagtcagc    3420 ccttcttct cacgcatgat ttgcagcttt gtttttgtca tactacctcc ttattgctg    3480 attgatcata ttctaaaatt ttttttgaaaa tatcatccac taattcttt ggtatgtttg    3540 atcgttcgtt gtagtccttc gagaaatgac cccaagccac ttcttgcttg atcacctcat    3600
tttttaaacc tagaaaaata ttacttgcga actttgtagg cttttgtaat ggataatcat    3660
agttgttata cctggttaaa ttcttatatg gtaactcaaa gcctataatt gtttcgatat    3720
actcccatat ttttccgctt gcgggattct caatcacaaa atattttgga ttgtatctct    3780
tgatgatttc aatcgtatta aatacacaaa gttcaccatt tatccgagta ataaattgct    3840
tgtgatactt caaattatta tgagactctt cataatctct tttacttctg attgtaaaag    3900
ggcttggtgt catttgtggt tcaaacaagc tatcagatat atcttcacgt ttccaacatg    3960
cattgccatt ttttaaagca cttgcaacac tccagctctc acaaggtgga cttgcaataa    4020
ttaaatctgg ctttggtaac ttatccaagg tttcaaacat aagattattt ccaaacatcc    4080
tagagtaatc agcaagattc agattaataa agtgatggtt tttattttca atatccaacc    4140
caattgaata tatttctatt tcttcaaatt catcagcaga gcgtttataa cagccgtttc    4200
cgctgtcaaa taatgcccaa actatcatac tgtccaatcc ctcctaagca atttgcatta    4260
atgtcgcaat cattttctga tcgtcttttt tctgtaattc atccaggaca tgggcatagg    4320
tttcttgagt cactccaaca tccgcatgcc ctaatcttgc tgaaatactg tgaatcgaga    4380
```

```
cccctgcaga aagtaatact gatgcatgtg tatgtcttaa cccatgacaa ctaatttctg    4440
ttatccctgc ttctttacat tttctcgaca tgaaattatt gattgtcgaa ttaaagtatt    4500
ttttatagga cccatttttcc aattttttgaa taaaaatagg ttcatgtggt ggcaaatctt   4560
cgagtttcgg cttcagtagt ccgatagtct gccaatccaa tgttattttt ctgactgatc    4620
cttttgtctt tgtgggttta aaaccaccat gaccagactt ataatcccaa gtcttatcaa    4680
tggagagttt attttcagtc cagtcaaagt cttctggtgt aatggccaag cttccgcaa     4740 atcggattcc tgttttggca ataataaata ccatccaatc cacgcctagc tcattattta    4800
aatcaagagc atgcatcaac ttttgcaatt cttcaacttg taaaaacttc tttttcttgt    4860
ctgtagatgg agttttgcct tttatgactg ctcgataagt tggatcaact tcaagttgtc    4920
tgtcatggaa taaatctttt atacatgctt ttactaagtg gtgaaaatct ccagttgttg    4980
atttctcatg agttttagca tactcattaa gaattttttg atattgcgtg cggtcaaagt    5040
ctgataggag taatttcgga catgttttttc ttaaaaattc agatactatc cgatacttct   5100
tcaaagtgat atctgaaata tccccgactt tatatatttc tatccactca tcatagcaat    5160
ctacaaataa tttttcttttt tgttttctct tagtcaaata aactcatctg tccttccttt   5220
tcttctctaa gtggaatcca atctgggaat ttactttcaa tatgttcaat ggcttcctcg    5280
gtccattcct tgattcccaa aaactccatg gcatctttgc tgtgcggaat aacatttact    5340
tctgaaaagc ctaatggatt atcagcacta ttttgaatga aatatacttg cttcgctgcc    5400
atttctaacg catctccatg aataatcacg ccgttcattc cacgaattgc aaaggcatga    5460
atcaagaaag aaatcgcttc gtctgataat tctagagctt gataccaata gttactcggc    5520
aaatagttaa aaaagtcagc attcattcga tcattttgcc attttttgaat aattagcgtt   5580 cctgttcctg ctccagttaa atcagaacct ccagaaccac ctacaagcaa cgctgtgagc    5640
ttaccaagtg aatctggtgt ataatgctgt ccttttgatg aaacagctga gtgagtcata    5700
aaataatctc tgaaaaaatc aatactcatg tcatggtgga tatttaagat tttagagtaa    5760
aattcttcac gtccttttttt atcaaacaca agttcttgaa ttcgatttgt aaaattcata   5820
tgctcatcaa catcgagcat gtcatagaat tgctgctcag taattgtcat catccaccac    5880
tttcactaaa tcaactccga gggctttgcc tgcgaggtag gcataaatga taggcatata    5940
ttcatcctcc ttccttttat tgcttatatt ttgcttttta agcacgttta tctttaatta    6000
gataaattgt tcattggact atctaaactc tcaatgtaac cgtaactttc acgaattaga    6060
gctattccag aacgataact acttctttca agttgcgatc aagaaaatca taagttgta    6120 accaagtcat ttgctgcccc ttattgaaaa ccgtccgaat atctttgtaa tattggacta    6180
gctcttgctt atacttctta cgagcatcaa tatagataat cttatggccg tatccgtcat    6240 actttgctttt cttggccata ttgtagagct tcattaatgg tatagggtta aaagccgtca   6300
tcgcttgcct cctctatttc tatatctatc tggttttgt ctaggtagta ttttttttgca    6360 atgagtacta ctatctggct atcatctgtg taataaccta actttgtcat gtagtcttgt    6420
atatttttca tgagattatc caagtctggt cttgtagttt tgaattgcca ccactttttc    6480
ttttgcttaa tcgcattcca aaatgtcaca gtgagctgta agggcacatc tttatcatat    6540
ggtttacttg gagcattgcg ctttagtgca ttgacaagtt ccttattttc agtaccttttt   6600 cggttataaa aagatatttt cccgttccta tagccaatac ctttttgttg ttgcgtaact    6660
ggcatttttt ctaagttgaa agaaaacttc attttccaag tctcgcaatc tgtttacgga    6720
```

```
attctttatg aaaatactta gtttctttgt tgttttctct agctcttttc atggcggtca    6780
tctcttcctt agaaactctg tcctgtacta attttctgc tttagttggt ttttacataa    6840
tttactccca tgtgtataca gctggcatat cagccatgtc agctaatttt tgatgagtt    6900
ctgtgtaaga aagttgctca accattttc gttttacaga cttgcttaat ctataatttt    6960
cttgctcaaa agcattgatt aaataatgtt ttagcttatt tgccatttat cgtttatcct    7020
taattccatc aaaattgaca acactatccg ttgaatctcg tcctaagcga cttacaatct    7080
taggattgta cactgcgtta gggtctgcta ggttagtcgt tgtgataata caagggtttg    7140
cattgaccat cgcaaagagg aaacgttgaa cataatcaga agcttgttct tttcctgtga    7200
atgtactttc gcttcccaag tcatctaaga caacaaggtc tgcacttcta attaaggtca    7260
atacgttttc ttctgaccaa taagagtgag ggtcgcttat acttgcttta agttttctaa    7320
acatctcgtt agcatctaag aataacactc gcttgtttac tctgcgctgc ttagcttgat    7380
cgttcaccca ttgagcaatt gccatagcca gatgcgattt accagctcct ggagaacctt    7440
taaatatcgt gttgaactct tcaccattta ggtaacgcct tgcaatatca caagcttttt    7500
tgagtactac tgcttcccca tcgttgtctg tgttgtattt gaaattagta aagttagctg    7560
tgagaagcga tttatctggg acaatactgt ttttatccaa cacagctgta gtcttggctt    7620
cgtgttcctt acgtttctgt tccttggttt tcctatactc agtaataatc gaaccctcat    7680
agtatctgag cgcttgagaa taccctggta caattgactt ttctctgtga agaatatagt    7740
tgtttaactc acttaaattc ttatcaacaa cctcatctgg aatctcatta gatacaatga    7800
aatcccacac ttcagcatca gccatcactt tttcttagc aagatttcga gctgtatcga    7860
ctttttcttg tatttctgga gataaatcaa ataatccccc gcctcttttc attaccaccc    7920
cccacgatca ttgacatcga acttcgcatt tggatcagca aatactcctt gacccttatt    7980
tactggtttt tgattgaggt aactttcaaa cttaggtcca aataatgtct ctggacggag    8040
aaacttactc atttttcat cattacccca ttcagcaact tttatatcaa ttactcgttt    8100
aaagtcatca attgtaaaag tttcattgaa tcgagcgttt atcaaagatt gcgtcttctt    8160
gctggaagct cgatagctag tgcctgcttt ttcattgaga taggacaaga ttcccttaac    8220
atcgtcgagg ttactcgaca atatattatt cttatctaat ctattcttat ctaatctatt    8280
cttatctacg tcaacggcac gttgccgttc cgttaacggt tcgtcaacgg ctattaaatc    8340
cgcatattta ctgggtttgt aggtatcttt tctaattgtg ttttgctctt taaagtcaac    8400
aataaagtag accatttcgt catttaaggg tttaataaat tgttttacta ctaataaacc    8460
taaactatct tctgcagctc caaccattct tacaattggg aacgcttcga ctactccgtc    8520
atcatctgca tttaacataa gatgaaagta taatgcttgc gactccagag gcaatcttaa    8580
gaattttga gtttgaattg ttcgtttatc tatcattctt cgttgtgcca tatatatttc    8640
atttccttat aaacaatagg ttagcgctgg gtctccctga gtacatagcg cccgacttac    8700
atgtccttcc cgcacaaagc ctagtgtctg ttatttagaa tgggagttgg tcatcgctga    8760
tttccatagg agaaccgcca aatggatcta cttgcggtgc tgcttgtgac tgttggccac    8820
cacccattga agcgaattct gagcgacaca agtagttttt aatttctgtc cctgtagcag    8880
cttttcttc tccattttta tcgatgtaag ttcctgtacg ctctttcaca agaataaata    8940
cacgttttcc tttgaggaat ttaagtgtct gttcgttgtg tccgtaatca atcggggcaa    9000
tttgttggtt gttatcttcg atacttgcaa gaatacgttg caaaccgcta tcagaccatg    9060
gttttccgaa taagaaccag ttattagcag tttccccatt gctaccttca atatcaaatt    9120
```

```
taaacattgg atcaccattt ttagattgtt gattttttcac atcaacaata gttgcgatgt    9180
gtacgcctgc tgcgaatcct tggcctgtta agttgctcat ttcatttctg ttatattgca    9240
ttattttttgt tctccatttt cattagtttt cgttttttct actgtttgac caaatttaaa   9300
taaatcttca attttacaag ctatgcgatc atcaagtcga ttttttgcat aaactccgtc    9360
acttccttgg agtattgctc ctcttccgtg agttgctggg tttacttgaa tgcgacctac    9420
tacatcagtc agtcccaaaa gttggttaat aacttgattc cgtacgtcag gtatatattc    9480
agtcagcttt gtgccatctt ccaaatctac atctctctta ttctcccaag cggtaacata    9540
gatattgata gggaatgaat aaatcattgt gattagtctt agaaagtaat ttgtatagtc    9600
tccgtagtct tgaatttcat tacgaatacc attcttactt ttaaggccac gtgctacgaa    9660
ccaatctttt tcaaaagctg tgatattatc aataactaaa gtttgataac cttcaagaat    9720
tcctctggct tcatctaaaa attctttcat tgattgaatt ggattttctc gattaaatga    9780
aattacatca acaccctta atcctgctaa taccctactt gatccatcta aatcaagaac     9840
taatactttg cccgtcagtc ctttaattgc acttgtttta ccaagtcctg gtttcccata    9900
aaggagcact ctccattcat gggtacggct tatatccgtt gctttttttaa tttctaatgc   9960
cataattaaa acctcaaact ttctgattgc tgcaactcaa ccccttcaat aactgctcca   10020
ttcttcaaat cttcaagcat ttgtttctta tcaagcttag gtggttgagg aataaaatag   10080
ttatcataga actcgttctt cataaattgc tcctcattgt cgaatgttaa ggactttgca   10140
ttcttttgga tacgaatatt gaatactgcg cttttttattt tgtctattcc tactacgatc   10200
atgctatttt gtaggtagtc tttcagacct tgtttctttt taactactgc ttttttcttg   10260
tcttgaagtc gtttgatttc agcagccaag gctacttcat cggcttcaag gttttttaca   10320
acatagccaa tatttatagc tttgtctttta atttctcctt cgatactctc taaagtatct   10380
gcccacgttt cggcatccaa gtcctccata tcatagactt gttgccaatc ggcggttaaa   10440
tcgtataaac tcattttttat tcctccgaat ttttgttata atcagagtag aatctcgcaa   10500
agtttctact cagctcactc tgcaaagtga gcttttttat ttttctctga actcgttgat   10560
atcaacttct agagcatctg ctattttgca taccgtttca aatgaaggat tatcagtctg   10620
ttttaatttc atttgtgaaa aatactgttt tgatattcct gtcattttttg ataaacgata   10680
agtagagata ttttttctctt gcattatttt ttctatttta ttccacatac tatatgttgt   10740
attgaccttt cttgatttaa cgtttaatga cactatatat agtaatatcc acttgactaa   10800
atatagtaat tcttgttaca atatacttat gaatgacaag ccgtggttgg taagtttatt   10860
cataaattca aacagaaagc tggtacctaa tgatgggcca ataccaaatt acacatgtcc   10920
gggtttcgga cgataatgca acttctgtag agaagattac tcacgttcaa cttaacgatg   10980
gaactccgtt cacagtttct caaatcgtta attttattga taaaggtcat gattttttct   11040
acactcatgg ttactttctt agtaaggctc ttgttgaagc tgttcaccca actaatcgtg   11100
atccgtatat ccgtactaag gcaaattcaa caactaatga taatttactt aatctaccaa   11160
ggttctaaga gcacacccat tactttttgtg atgggttttt attttttcgat cttagaacgg   11220
ttttcagata ttggttcatc aacttcatac ataaaagtaa ccaattgatt aacttttcct   11280
ttagttttac ttgattcatt gctcagtgcg tattcacctg gagtaacttc cccactcaat   11340
gtacgtgcta aaatttctac aagttttttct tcaaatgttt ttgatttcat atttttctcc   11400
tctcctccta gttgctgcta ggggcttttt atttttgtcat aaatcgtaaa aagtctagta   11460
```

-continued

```
aatagaaaaa ttttcgttct attttttccac cagatacaat ccaaacttgt ttatcaggcc   11520
atgctgttac aataagacca tcagttgttg tgtactgctc aagcactctg ctcccctct    11580
cttttttcga tacccgataa gataattctg cctatttcta tagctatctc tccagtcaat   11640
ggattgtttc tgcaccactc tggccaatct tcttcactga ttcttgttcc atcagctaag   11700
atatttgtaa ccttgtactt tttaggtggt ctcctttgtt ttcccatctt cattcctttc   11760
tatgcactat tgcatgcaaa cgttctgcga taatatttaa tggccaaaca tttgcacatt   11820
ttcctgcaaa aaattcgtat acgatttcgc cagtatctat gacgacaatt tgatatgtga   11880
ttgtttgcat ggtataatat ccttatctaa attcatctag ctcactgttc ccgcagtggg   11940
cttttttgtt tatgcaactt cttgttcaac tactggaagg tatcctgccc ttttcaactt   12000
acgatacaaa aactcacgcc ccttttgagt ccaacaagta ttgattcgtg tatgttgctt   12060
gttgtcattt cctatatagt taaatgttcg acttctgata tagcctttgc cttgatacct   12120
tgagtacaac agccactgat tattttgctt atattgaatt cttagtttat tcaaaatttg   12180
attaaattta acagcgctca taccgtaatc ctgagcaatc tgcttaacaa tcaactcatc   12240
tgggctatct aagattaggt caagataacg agttttttct gttgcttcag caagttctaa   12300
attaagctga ctattttctt tttcaagtcc aagccgagct tgtcgctcat ctttgagttg   12360
tgttgcaaga tcgattaata tatctggatt aagtagcgct tcttccagtt tcgcatccgt   12420
catatatgct ccgtgcttgc ggattgtggg caggacttct cttgttaccc actttctaaa   12480
tggcttagca tttcgattat tggatcgaag caagatttga tacaatcctg attcattaat   12540
aatattttta ggacttcctg accctagact ttgtctagac ttgtcctcat catcaacgag   12600
ttttgctaag tcagttggat ttgttgcctc aatagctttc gcaacatctg ctactacaaa   12660
ccacggttca ctttcgataa gcactgttcg tacttgtaaa ttgttgaaat taaaattttg   12720
taactgattc atgttgttcc tttctaactc accctttca atttgtcaag ttcttcatca    12780
aattttttta caacctccat tagttgcaaa atcctactc ctgtaacttt tgacattgtg    12840
cctaatcgaa cagccgaaat tgtattagga tactttctta atctataaaa tacatcataa   12900
gaaatacccca tccgttcagc aataacttcc atacgaagac cagatccttt tagcagatca   12960
tcaagtggct cataagtttt tttctctgcc atattgacac tcctctctat atttatcaaa   13020
ctgctactta cgtcgaggtg aatacgccgt gtacctacat ttgtatatca ttccgtctgc   13080
cgtactaaat atactatgtt cgttcgctac gcttgactat gaactcatta taaaacaacc   13140
tttacaattt gtcaagttat aactttgcaa attgacaagt ttttttcttt atgataatat   13200
ttatccaagg agatttacat atgaatgata tccacctcgg agaaatgatt aattactatc   13260
gtaaacagaa cggatggacc atgaaggaac tcggtgagaa aatgggcaaa acagagtctg   13320
ctatttctct ttggataagc aataaacgaa gtccaatggt agatgattta gataaactct   13380
caaagctatt taatgtttca ccagaagttc ttatgtttgg aaaggtaacc tctcctatta   13440
tagaagatac cgttgaaaca atgaaaaagc ttgatgaacc tcgtcaacaa gtagttcttg   13500
aaactgcaaa tattcaactt aaagaacaaa aagcaattaa acgtgagaaa caaatattac   13560
cttttaaaaa agcgcaacta gataagataa ataatcttgt accttacgat catgaacaag   13620
aaggatttgc tcccattatt ggtgaaattg ctgcaggtac tccaatattc tctgaacaaa   13680
attttgaggg tatgagacct gtttatggta agtatgccgg acgggacgac gtattttggc   13740
ttcatgtaaa aggggatagc atggaaagtg aaatacatga tggctccttt gctctgatat   13800
tattatcccc tgacattgat gatggagcaa taggggcagt aagatttaca gatgataatt   13860
```

```
cagccacttt aaaatgtgtt cattatgaat atgatgatgc tggatacgtt aagcgcatta   13920
gacttgaacc gttaaatcca aaatatccaa tccaatacgc agatgaatcc aatcctgctg   13980
aaattgcagg tcgactagtt aaagtggaac aagactatta attgtggagc atatatgaag   14040
tttggaatga gaaacccag tataaaaaag agttttaaag ctcgaacaac tggaaaagtc   14100
aaaagaaaat ttaaaaaagc cctaattcca ggatatggaa aaagggcat gggagtcatt   14160 aagaaaccta agaagcaat gtataataaa gtttatagaa agacaacttt ttcttctgg    14220 aacctattta aataaaaaat acgtgcgcta accacgctaa aagggtaagg agaaatattt   14280
tatgaaacac agtacacctc agactaagaa gccaatttac aaacgtattt ggttttggat   14340
acttgtcgct gtaatcgtta ttggagtagg tggagccctt gggggtggat ctgatgacaa   14400
aaaagattct agcacttcta attctaccga gacaaaacaa agctcaaaag aggaaaaatc   14460
tactgaacaa agctcttcag ataaacctaa aaatggttgg actcaagaaa tttatgattc   14520
aatcactgta gctaaaatgg acttcgatgc taacggcaat atgtcttact ctggtggtac   14580
tccttatgct gatattgaag ctaaagttgg taagcctgat agttcttctg aaacaagcgt   14640
tggtgatcaa acaacagtca ctgcaacttg gtcttctgtt tcatggacta aaggaacaat   14700
ggaaagcatc actgttcaat atgacaaaac tagcggacaa atcacaagta aaaataaatt   14760
taatgcgtaa ttaaacaaaa aaaaaaccgt cctgtgactc tccaaagttt aggacggttt   14820
taaacaataa gtgtagaaaa tttacgactc acgtattttt tctatactct attatatcaa   14880
atagaggagt aagagcacaa tgaagaaagt agcaatttat gttcgagtct caactctcaa   14940
tcaagctgag gaaggttatt caatttctga acaaaccgac aaattaaaag cttattgtgt   15000
tgcaaaaggt tggaccgttg ctgaaatata caccgatgca ggattcactg gttcaaatat   15060
tgatagaccc ggactgcagc aacttataaa tgatatatca gtacaaaaat ttgacaccgt   15120
acttatttac aaattagatc gactatctcg gagcgttcgt gacactcttt accttgcaaa   15180
ggatgtgttc gcaaaaaata atattgactt tgtatcatta agtgaaaaca tagatacatc   15240
ttctgcaatg ggcgggttgt tcctaacaat attgtcagca atatctgaat ttgagcgtga   15300
aacgataaaa gaaagaatgc agctcgggaa attaggccgt gcaaaatctg gaaaatctat   15360
gatgtggtct agaacagctt tcggttatt gcataatact gatacgggag ttcttgagat    15420
tgagccatta caagcagagg ttgtaaaaca aatcttccaa gaatatctaa atggcatgtc   15480
cataactaaa ctacgagata aattaaattc agaagggcac actggaaaag ataagccttg   15540
gtcatataga gcgctaagag cgacacttgc taatcctgtt tatactggca agttaaaata   15600
taacaatcaa atatttgacg gactacacca agcgataata agcccagaat tattccaagc   15660
tgtacaatcc gagttagaaa ttagacagaa ggaagcatat cagaaaaata ataatccgcg   15720
accatttcag tcaaaatata ttttatctgg aattgcaaaa tgcggctatt gtaaaacacc   15780
actccaagta atactgggat ctgttcgaaa agatggatct agggatatta aatatcaatg   15840
caaaaataga tttccccgaa aaactaaagg ggtaaccata tataatgaca ataaaaaatg   15900
tgattctggc ttttattata tgagtgatat tgaagcggag ttattgatc agatttctct    15960 tctacagtta aataacggtg cttagaaaa tctaatatct ataaactctg aaccggttat    16020
tgatacaact gagttcgaaa aacaactgat aaatattgat aacaaaataa aaagattatc   16080
cgacctatac attaacgata tgatttctct tgttgaaatg aagcaagaa gtgagaactt    16140 gaaaaaagac agggatgctt taaaagccaa aataacatca tctaataaaa ccagcaccac   16200
```

```
tgatcgactt aaaaccgcaa gaaagttgat tgggaataag cctattgaaa gcttaagcta    16260
tgaccaacag aagaatatca tcaatcgcat aattagtcgc gtatatgtga cagctgagac    16320
tgttgatatt acatggagcc tataaataaa acacctaaat aaactcttta ttttttttgaa   16380 aataaagagt tttactatcc ttcatttcaa ttaaagatag tgaaattctt tatttcagtt    16440
actttcttct atataaatga aaaactcccc catatggagg agtaaattga attgtgtttt    16500
tattataaca aaaattccc aaccgaagta gggaattacc tataagaaca gacatgtaca     16560
ttatagcata ttttagattt tttcaaatag ctagttttgt ttgttctaga tttaatactt    16620
tagcgaatag gatttaattg agaaaataag aattataatt tgcattttca aaaaaaatca    16680
tctatactta aggtaagaag aataacttgt gaaggaaaac gactgggtcc caaaatgggg    16740
tagctgtaca atcagtgagc attcctatgt acctggggtt attcaaagct ctccgattgg    16800
agagcttttt ttattatttt gattttaaac tgtcaacaaa cttttctgga tttttcttaa    16860
tttctgaaac aataaattct actaattgtt cagagtatgt acattgttca ctattaccaa    16920
gtttatgaat gtatgtatat ttcttctcct gctttatatt ataaaaatcc ataactaaat    16980
tcaatacgta tgaattaaat ccttttagcgt aattaagttt tattgactgt ttttccaatc   17040
tttttctaac agccataata acagaattat atgtgtattt atgagtatcc gcaggatctt    17100
ttaattcttt aaccatcgcg acattgctct cagcatcttt atgtattgct acaacaaagt    17160
ctgcctctga ttttttcttt gtaatatata aattttgttt aatacctatc gcaaatttat    17220
cagaagataa ttctgtagcc aagacatcaa tatcattcgc ttgttgaata aatttctctg    17280
ctatttcagg gggatatttt attttaattt gttcattagt aagcggctca tatcttgatg    17340
atatggtcaa aaaattttga gcaatatact ctgtgacatc tttgctatga aatctttta    17400 gttcattagt ataattcaat acgcacgctt gaaaaagagg agcatatttt aattcatagt    17460
cttctgttat atagtgcgta cttatatttc taagttcaat aatttttcc aagtttattc     17520 gtaatatttg attttatcg gtatatatct ttgatattac agcactaaca gctaatgttc    17580
tttcaggatt atccggataa tatatactct ctcctctatt caataattct gcttttaaca    17640
ttaattccca ggcattgatg ataaaaaagg aaaagccttc aatcctatat ctcagtgtag    17700
gtttattgta aagttctaat cctactatga aagcttctac gcttttatct accaatctat    17760
catttagcat ttccttcata atcttgttct tccgtttagc cttttattt tattatatca    17820 taggttttat cagttaatcc aaaaaactcc cagtcacgga accgggagct aagaaaaaca    17880
aaattagaag caagcttctt cttttgataa ttgtattata tcactattca atctctagac    17940
aaaacaaaaa aacatccgat caattgaccg gacgctgtgc ttttaccaga ttacattctt    18000
ttcatcgaat tcaccttttt taccgaacag ttctgagctg taaatattat ctgttttcaa    18060
attcattttt gcatattgat tttgataact cgcaagcata cgcggggtac ggatataacg    18120
taaatgtgtt ccatttgaga tgaaccattt acctttgtgt gggcctgttg tatctacaat    18180
ttttaataac atcatttctt cttcgtctcc tttgttattt cctgagtttc cattacttgc    18240
atcaccacta gatgatgcat tccctttaca attcgcaata tcattcgcaa attgctgttg    18300
tgtgatcccc cactttgtta aataaggaat cgggtccaca tggtctgaac cgttgttagg    18360
ttggttatgt gtgcaataat tgtgtgtttt gatacctgct aaatctccag tatcaagtgt    18420
ggttggaata cctgcttgct tggccaaatc ataagaagt tcacagtaga ttttataatc    18480
tctcatgaat tcctctttg aaccgtgact ttcaataagt tcaactgctg cataggtttc    18540
atagttgtaa cttccaccaa catcccatgc cccgcgattt actggggcaa cttggataac    18600
```

-continued

```
ttgaccattt cccaccacat gggtataaaa tcccgtgttg aggtccttac ggctcatata    18660
gtccgcttca ttctgtgcag tactcccagg atttccagtt gaatgtgcgt gaacttggga    18720
atatggagca tagccaacct gaggtgtatc agttcggatt tgttgtttaa tgttgtaaga    18780
catttaatcc tccttaaaag tttctctatc taatgcaatc tcgctatctg aaataccagg    18840
tgttgttgga tctgcaacta ccccaataat tgctaataca acaaatactg cattaacaat    18900
agctgctagc tgttgattaa gaaccacaaa gtcccattca tagccaaacg gtgcgccaat    18960
ggtttggacc attaataaaa gcgccggtaa gaaagccagc caaaacttag cacttagcag    19020
tcgtaatttc caattgattt ttgtcatttt tattttccct ccatcattta aatctttgtt    19080
agaaagtagc aaataattgt aatcccaagg ccaatcatat agccccaagc ccatttgtta    19140
tttgcttcaa tctttgaaat atctttagca ttatttatag ccaaagaata agccttatca    19200
gctttatctc gtacagactc ataattatct agctttgttt caattcgagt agtccgctct    19260
aggatttctc gcactgcttg ttcttccaaa tcttattatt ctccttcttc taccacagga    19320
acaactggag tttctgcttc tgattgcatg ccagctctt tagctttgtc aaaaagttgg     19380
accatgaagt cctaacatc ttcacgctgg gtttcattac taaagaactt ctctgagttt     19440
aaaagattca tttccaattt aaatgtacca ccatcatcaa tggccgctgt catttcacta    19500
gtcgtcccac ttcatcatc agtactacct atatacctga aagtattct ttttaagata     19560 tccatatttt ctccttatta attttttttaa gacacattag gtatagctcg ataagttata    19620
gaaaaacctg cataacaatt atctttagct acactactag taattcctat tcgcccatct    19680
gttgttattt taacggccat attttgtgcc ccacccattg aacttgctcc gcttgcaatc    19740
tcatattgag gccaaacact ttttggtaaa ctaccaaaga acctctcttt atttgcttca    19800
aatttccccc agttcccacc acctgttata tagacaatat taaaagaacg ttcatagttg    19860
actgtcgctg ttattccttg ccatgataac ttcataggaa gaacatcgga actcataacc    19920 atacccttt gtgtataaga ggcagtctca cgtagacctt cagtgttata tctagaaaca    19980
gtcattccag atggagaaac ttgaagtgaa ccaggttttg tttcatcctc attttcgaca    20040
taattcattc ttaaaccaat ctcatctata acaagagttc ctttggtttt tcctactgaa    20100
gaatcatact caaattcatt tgtgattttt cctgctctta catctcctaa tattgagttc    20160
actgccgaaa ggtctcaat cgttgctgag ttaattttgg caaaatcaat agccgcatta    20220
gcaatcatgg cgtttgtaat ccaagcattc actgcttgaa gattcgcagg attcaaaaac    20280
cagatttgcc atgcagtacc attccaaaca taggtcatat taggttgtac agtaatacct    20340
tccacattaa gcggttcagt tcctgtgtac tgccaaagca tatcctcgaa gcgttcttcg    20400
ggttctgtat cttgttggac gacttttccg ggttcgccgt cattaccggg cttaccttct    20460
tcaccaggtg gtcctattgg cccttgttct ccatcttgcc catcattacc cggcttacca    20520
ggcgcaccat catttacatt ggtaattgtg acgatgctg tacctactac tgcaccattt    20580
attttagcct cataagaata aactgctttt tctggtacac ttgctgcact taccgttatg    20640
gcttgagttt gtgccatcgg cgtaccgtct ctaaaccacg tataggtatc tgctacagtt    20700
tcaactgcat ctgctccttt gaaatgtgt gcagacaaat cagttgttcc tgtaccattc    20760
ttaaattgaa tcccattagt agtcattatt tcagaacgat agggtgtatt ctggtcaatg    20820
attgattgca tacggtcaag gagatcatca gaaacttcgc ttttcaactt gatgtaattt    20880
gagaaagtga ttttattatt ggttggattc gtaaagctta tttctaactc agaaactcga    20940
```

-continued

```
gcggataaga agaggcctac atctccattt gaatccatga aattcatgtc ttgaattcga  21000
acagtatccc caatatgaag cggtgtgcca tctccagtac ttgaaacagt caaatcacta  21060
gtcgctgtta cttcataagt aattaagggg taagcatatt gcttcagttg acttaatgca  21120
tagccccaca ttgcattaac tgtagtatat tcggttgcta cattttttatt ggtaaaatata 21180
tcgccacttg acgatttaag ctgtgagggg aacatctgag cagatagcgg agctttagca  21240
taactttcac cagctctttt atagaattct tcttgcccctt ctgaattcgt aactgaccag  21300
gaagagtttt tccaacttaa cccatctttc ccagtgacat aaagtgaatt aaatatctga  21360
gacttttcaa cttttcgatt aaccccgtg acattttcgc caaaggataa aagcacatca  21420
tttctatttt gaccaactcc ttgaacatcg ccaccatcat ttttcttgta aatattgagt  21480
gtgatattat caagcgttcc atctctttt aattttgtga caaactcaaa ttcggcatca  21540
aagttttgaa tgactgaaat taaacgagcg agtttagtat cttccgaatc ataattaatg  21600
acccttgtat catttttaac ctgattaata ccaagtgaga ttttagcgaa attgattagg  21660
cctagttggt caaagtacca ttggatattg tgactggcag tatttttaa agccttaact  21720
tcttcatttc gcatttcaag attaagagtt agacaattga agtaattttt gtcatcatct  21780
tcttcaacaa tgacagaatc aaaaagaaag tcttctccct catactgaaa gctgaaataa  21840
gctcgctcat ttagcaattg aacgtaatct tggactactc catttttttat tttattgacc  21900
gtgaaatcaa aagttgatgc cccctgtgct aagtagcgat gaaaattatc atctttaaaa  21960
tcaggagttt ccgagtcgtc attactgagg aaaccaaccc gtttcaatgt atggtcatga  22020
attgaaatta acattataag attcgctcct tccactcaat ttcaacttta ggcgggcttg  22080
ttgtgaaatt tgaatacaca atatctagcc tttgacttgc tcctggagga attgaaaaga  22140
attctgaacc cgtgatatag tctgagttcg cccctaagtc attaactgtg attttttgatt  22200
tttccatatc aacctttatt tcatcttctg gttggtattt attaagaata tccacagtat  22260
actcattgtt tagattcatg agtttaaatg atctaagact tgtatctgct accatttgat  22320
aataccgtct tttcccgatc acaacataaa cataagcaag tttggtagat gctggtacat  22380
cacccatgag ataagtttca gccatcgctc gccagtaaaa agaaatcttg tttccttgtt  22440
tgataatcgc ctgtccgcca tgacttgcag caaaaagtgg agcaccgttt ttatctagtt  22500
ttccagttgt cgctgagaat gtatggtttt tgaaatgttt taattttttta tctccaccaa  22560
tcagccaaaa gttcaaactt gcactttcac caacgcctcc tttatagatt tcaaagcaag  22620
caagtggttg cttgttttca tccgcaaaat gaatttggaa tctgccgcac tgttcaaggt  22680
tcttttgaat atatagtgta ttgaaattag catgccaatc tttaacataa ttacccaaat  22740
catctttagg tacttcatat cttaaaactc ctgcgttcca aagcgaagat tgcgccattg  22800
ctgcaattcg aatcccatca tctttccaag cgatggtact atttaatggc ataccatcaa  22860
gatttgttgg ccatgaagtc gtccagcttg tatctggaac aaagttagtt tcaaaatcag  22920
acttagtttt aaaatcacag actagctttt gacttttagc ggtggttgta tctgcttcat  22980
ctggattacc aatttcaagg attccgttttt gcccaacaaa ggctaaatag cctgtttcag  23040
atgtggagt gactttaatt gtgggataga taggcaaggt tccattatta ttgattagta  23100
ccgaaactga gtgatcagca ttatttatga tggttccatt ttctccgcct gagttatcat  23160
tatttaacgt ttttgtatcg actgattctg cgtagccttt aggtactaaa aatgtaagtg  23220
taccagttgt atatttttcca ttattatgtt cagtagcttt gatttctcca tcaataatca  23280
cttcccaaaa cacattaggg tcatcagaaa atataaatact ttgtaactgc ttagagcttg  23340
```

```
ttatttttcc tacaattcgt ttagttgcta tcaagtcttt tagtaaagta aagtcaattt    23400 ctatttttt tgatgaaagg ttagaactaa tcaggttaga tccatctcca accttatttt    23460
ctgtaacgtt tgtcattcct gtagatatac cacgtcgaac atcgtttatt atcatgtaat    23520
ccatcaattc aacgttattt aattttatcg agttatattc cattgattaa acacgtgccc    23580
cttctagcat ttttgcgata tctccaagtt tggcttgttc attgctcata tctttagcaa    23640
ctgctgcagc aaaagttttt ccatttattg ttaaatagat aggtctatca ttcaactttt    23700
caaccgaatt aatcaccta agaagtaaat tattggtttg agtaccactg ttactatttg    23760
gtatgttgtt tgcagaaagt aatgtataag tttgtaagtc aatatttttt tcaagtaaag    23820
cactattatc aaattcggta gagactggta atgttactcc tgtgcctacc aaactttgaa    23880
gattatctgc tacaccagaa atattttttt gaactgattt aaagttttcc atcaagctat    23940
cattgaatcc actcataata gcttgaccag ctggaatcag tagttttcta tcataactaa    24000
ttggtccttt gtgctcttta atccaatctc caattccacc tacaaacttc ttaccagctt    24060
cccatgtgct ttttagacca ccaacaaatc catctataat agccttacct gctccagata    24120
aatcaatatt actcaaacta ttgaaaatac cttttattcc attaatgatt ccagaaattg    24180
ttgaagaggc gcctgaaata attcctgtta ttccgctcca cactccagac attactgatc    24240
gtaaaccatt accagagcca cctaagctac taaaaaatga tttgattcca ttaattgtgc    24300
cactaataga accacctaca gatgagatga tggagcgaat accactccaa gctcctgata    24360
tcacgcttct taatgctcca ccagctgaac ccaatcctgt aaagatagct ttagcggtat    24420
taatgattcc acctattcca ctaacaacag tagatattat tgattttata ccattccaag    24480
cgctacttat caatcctttc aaagatgtac ctgctgaacc aagacttgca aagaatccta    24540
ttgctgtacc tacccattga gctacagttg aaagtactgg tgcaaaagcc ttaaatacat    24600
tgactactgc agaaatgata ggcgtcaaaa atccgacgac aactcgaatt gtgtcaaatg    24660
ttcctgccaa tgcaatcatt gcaccttta atacaccacc aataaatgca cctaatactt    24720
gaaaaactgg cattaaagca ccagcaataa cagttgctaa aggttgaatt gcattccaca    24780
tttttacgaa tgaatttact aaagtatcta ttgatggtcc tataatcccc atcattgtag    24840
taatgccatt tgtaattgca ggtactaatg cagatataat agcttgaatt ccactaaaat    24900
caagttttga aattccagaa gagatagtgt caatcatcgg ttgtactgca actgatatcg    24960
cttcaaaaag tgatggtagc tgtccgaaag caacacttaa agtggaaatt actggcatta    25020
cagcagaaat gacattagaa aataattgtg gtaatttact aaatactccc ataatttgag    25080
tactgattgg tccaattgaa gatagcaaac tgtcaaaaac tggttttaaa cctgagacaa    25140
tagtttgaaa acttccttgt aggggtgata atatcgagct gaactttgca gtaaagtcag    25200
agaacccact cccgattcca tttcctaatt gtgaagaaag ttcttttccg gctgcactca    25260
caaacgtcga aattgctcct ggtaaagcct taaaaatatt tcctaccatc ggaatgaagt    25320
tcttgaataa gaatgttgat gtcgttgaca ccaacgcatt caatggccct tgcaaatcac    25380
ggcctagtga taagttcccc aaaacattag acattgcagc tttcattgaa tcaaatgacc    25440
cactaaatgt tgttgatgct tctttcgcag ttgtacctgt aatgtccatt tctgtttgga    25500
ttgcatgaat cgcttgtgtg atatctgaga gtttgaaat atcatacttt tgaccagtca    25560
gcttttgagc atcagtcaag agtcgttgca tttcttcttt cgtaccacca tatccaagtt    25620
ttaagttatc aagcatggta tagttctgct tggcaaaacc ttgataagca ttttgaatat    25680
```

```
ctccaatatt tgtacccatt ttattggcat tatcagacat atcaacaatt gcttggtttg    25740
acaaatctgc cgctttagct gtatctccat tcaatgattt aatcattgat gcagaaaaac    25800
ctgttacggt ttccatatat gcattcgcag acataccagc cgttttataa ccttctgttg    25860
catatttttt tactttatct gcattatctt taaatagagt ttcgaccccca cctaatgatt    25920 gttgtaaatc agctccttca gaaagtgatg aagaaattaa tttaccaagt gctgctcctg    25980
ttgctaccac accagctatt gcggcgacct ttaaggcaga accaattttt aaccctgcac    26040
tattccctgc cgactcagct tctgggtcta atatcccaga cattgaacct gatattcctt    26100
tggcagatgg cataatttgc ataagcttt gtcctaattc tgttgccatt aacttcctcc     26160 tccttttga aatagttgct gacgatattt ttcaaaatcc tcaccagaat gaaatcggat     26220
ttttctatca gttttttctt ttggtttatt gatgatatcg gtaacaagtt ttggcctatt    26280
tttacctttc tgaccatctt ctgttttaaa ccataaagac atacttaaac ggtcttgaat    26340
cccagctaaa agaagtgtat taattgggaa cttttgtcca ctcatcttca tttttatcct    26400
agattcttca ttcaaaccta tagaaaaaac agctatcttt agaggagata gctgtttgta    26460
atcgtaaata tgataaattt ctgcaaggtc gcacattagc gcttcttcat caaactttat    26520
cattctggca aggagaatta gttttttatt ttattttgag ctgcaaaaat atcttcaaga    26580
gtttctctga ttttgtcagt tgaaacaaag ccttcttcat ctcgaagata gttttttaaa    26640
tttttagatt gacgttctcc caataagaga tttaacactt ttggtaacag aagagggttt    26700
tcatcaactt ctgataaaat ttctaacaac tcgaaattat ttaaacgttc agttgtaatt    26760
tcataacgaa atccggattt tgttgttcct tttaacatat ttctcgcttt ctttatttaa    26820
tatttacagg gtcattagag ttaaacagct gtatcgagta tgtagtcgta gtgagagttg    26880
ccaactttat ctggtaaacc agtaagagta atctcaaatc caatagcatc agagtcgtta    26940
taagaaatat ctccaatttc agatactttc ccttgtggaa tcacaattcg cttaaatact    27000
ccatcacgta ctgtcatatc aatgacaacc ggatgctcaa taagttcttt tgaattagcc    27060
ttaaccgtaa ttcctgtttt aagggttccg gttacattgt cagccccgta tacttcttta    27120
agtacttcaa cattcaaagc ttcaattaat gtataactaa atgtgtcttc ttttctgtt    27180 tgcactgtag caaccgtatc gccaccccaa gctttgatac tatcagattt tggtgagttt    27240 ttattttta atccatcttc tgaaatatat cccaacggtt taaaagcaac atttagtgct    27300
gtttttgcat cagttggtaa agctgtacct tttggtgctg agtaaatagc accatcaatt    27360
ttgggctttg cagtagttac attttctact tgtgccattt taatcctcct aataatgatt    27420
aatatcaaat actgcttgat agcggtattc tttagtttct gtgtcagtaa agttgtagtc    27480
actgttcagt gatacattgc taatttcatt tagttcgatt agctgttcta caacttcttt    27540
caattgttca tttagctttg ctgcttcata catagaagga gcatagctct gaaacgcaaa    27600
tgttgaagat aaaaggtgat tgctcttgct actacctgtt ttttcaaata aaacatagct    27660
taatggcatc tctccttttt tctccaaaaa agacgatacc gataaatgag tatcaagaaa    27720
atttttaata ataatctcaa tcatttaacg caccgccttt aaaattgtat tgttttcat    27780 gttgtcacgc tttgcttgat aagtttcggc aaataccatt gcattagcac gattttacc    27840 aacatgcata tcttgaccat aacctggtcc acagcgctgt ttaacagcag atgctttttc    27900
tttaagaatt gcttgcattt ctggtgattt catcatacta gcaactccac tacgatttaa    27960
tttaaataga tttttagcca taatgttcca ccgtcacttt cttgttccag tctaatggaa    28020
taagtccctc gattccttca agtggttctc caaaagtccg ccacgtttta ccaaagaatc    28080
```

```
taacttttt  attttcccaa  tcatgagtat  ccttttttgg  aatagctaga  gtatagattg    28140 cttttttcc   tgtcaaagta  agctgattaa  caatatcatc  cgatgaagta  ggggaaacca    28200
agacattgtt  gacctcgatt  tccttatctt  cataaattgg  gtttccaaaa  gggtcttttc    28260
ctgtttctac  attgtcaatc  aaagttacag  caattccctt  aatcattccc  ataaaaatca    28320
atcaccccaa  atctttgttt  ttttagtcct  aaacggctta  attcagaatt  ttttatgaat    28380
aaaccacctc  caggaacaag  atatgaacca  gaaacagaat  aaccaagtgc  actctctgtt    28440
gtctgagtca  tgggttcttg  atcagttgat  gtcataagcg  ttctagcaac  aatatctacc    28500
gtaactgact  ttacaacact  tgcaaaatat  ggaggttttt  cagcaatcat  tacatctaaa    28560
gccctcccca  ctttatcagc  ttcttcacgt  aaggaatctg  agacaatttc  aagcaacttt    28620
tcagctcgtt  cttttcatc   tccctttaaa  gggcgccata  gcatcgttaa  atcatcaact    28680
gtagcaaaag  gattcatatt  attcctttcc  ttgctccatc  atcaaatcat  aaagcacttg    28740
tttgtttgca  cgtttatcgt  atttaactcc  aaaagcatca  agttcttgca  tgatttggtc    28800
tttagtaatc  ccgtcatagt  tcccatctac  atttgattct  tccaccactt  gctcttgttc    28860 agctttttg   gagtctgcat  cattagattg  gatatctaca  acagcttctt  tcgattcact    28920
ttcaagtacc  caatcgccac  ctgagatttt  aaactctgtg  tcgattgtgg  ctttagttaa    28980
tgtattaaag  tatctcattt  attacctcct  tattaagaag  cttcagttac  ccgagcaaat    29040
ttagtagcat  caaggatacc  ccaaccgagg  aacaactcgg  cacgaatgta  aacttggtta    29100
tatcctttaa  ggtcaagacc  tgagttgtct  gggtcaccgt  attggataat  ttcgagtggt    29160
acttctttcg  cgtaacccca  tttaaagccg  ttagcgaaat  ctccgatgat  ggcgcggtca    29220
ttttgcgtca  acgacatatc  agatactgtc  ttattgacat  ctactggcaa  gccgttaata    29280
gtgtcaggcg  ttgcgcccca  tttcaattca  gggaaaagtg  catttccttg  caagtctttt    29340
tgcttagcga  gggctgaacg  gaatgacgga  ttgattgcga  taccagtgac  atcagcatca    29400
acaccagtta  acaactctac  tgcgttttca  atagcgccgt  tgggatctgc  aatgcctctt    29460
ggagcttcaa  cttttttgcgt  aactttagag  tcaaagtggt  ttgtcccaat  aacagccgat    29520
gctgtaccta  ggcgagggtt  gacaccgtga  aatgccatta  agtcaatacc  acgagcaact    29580
tttttagcaa  aaccgtcatt  aaacgcctgc  aagatgttaa  ttttttcttc  atctgatgcg    29640
tacataaatt  cgtctgaaat  acgcgcaccg  tactcaactt  tgattggaac  cattgtctgt    29700
ggagcaagcg  ttactccgcc  gtgagttttc  ttgccgcttt  cagcaacgac  atcaatttct    29760
gaatccattg  taaacgtgaa  aacttttcg   ccgttgaatg  gaataggttt  ttgagctgac    29820
aagcgtgcga  ttgagctttt  tccagctact  ttgctgatta  ggtctgtgac  caattctggg    29880
tcaaataatg  ttcctttgtt  taataccatg  ttttattctc  cttctgtttt  tagtccatcg    29940
actaatttac  gataagctcc  atcttttccg  ccacccaaat  ttggttcaac  atctttaagt    30000
ggggcaggtg  gagtttgtgg  tttaatgaat  ccgctgaaac  gttcagcatc  agctttaagt    30060
gattcttcat  catcgcctga  aagtcggtca  gccaaatcta  atggcaaacc  agctttaata    30120
gcaatagatt  gtttgagttg  agttgttttg  taaccactga  tttgttttc   ataatcagct    30180 ttttcttgtt  cccaagactt  tgattcttca  atagttgctt  gatatgcagt  gttatctgct    30240
tcaagtgcag  caattttagt  tttgagttca  tcgtaatcag  caaaattagc  ttcaatcgtt    30300
tctttttggc  gtgccaatct  tgtttcaatg  atttggttta  actcttcttg  tgttttggt    30360 aaattgtttt  ctgacatagt  caaatccttt  ctcctgcttg  cccggcagtt  cggtaatttt    30420
```

```
tggtacaaaa aaacgactta aaaagtcgtc taataccgta tttgttgttt tttcttcggc    30480
ttgttattgc tacaagccca atgcgccaac aacgcactgt ccattaaact gatatccata    30540
tcatcaaatt gtgatttata cccaaatcca ccactagtac cgatatttct cttgtcacag    30600
ttagtgacta cagtagaaag tgaaggttgt ccagaatggc aaaagctttt ttgaaaaatt    30660
ccttgttccc atagggaatt agcattgata atttcttttta cagttggtag tatcggttct    30720
ttcaatttga atctttcat ttcactcgtt aagatacttt gaccactttg accatcaata    30780
acaactttt caacatctgc tttctttaag aaattaataa tccattggtt gccattcctt    30840
atggactgac aatcgattgt ttcaacaaat atcttccctg atagtgtttt aaccgcaata    30900
ctcattgcaa catttgcacc atcattccca tactaatac caacaaagag cttccctttg    30960
ataactggca aacgattaac cttgagcgca ttccattctt gttctgaaat gactgatttc    31020
tggttatatt ttggccaata accaagacgt tgaacattat gatccaactt atcttcacca    31080
agctcggctt cgatttacg ttcgtttaag tggtagccca tagatggatt agaattgtac    31140
caggcttcga catcatgaat gtccttgaca tcttcaaccg accactccgc ccaacctgaa    31200
tactttgctt tcccagctaa ggtattatct cgataatttg taaaaacagt tccacttgat    31260
actggtgttg gaggtgttcc acacattata gtcattggat tatcactgtc agtaacagta    31320
tatttcaatg ctgattcttg ctcagtagta tattcctgag cttcatcaat tactaaaatg    31380
tcgaatcctt ctccaagacc accacttgat gttcttgttc tgaactgaat tactccacca    31440
gattcaatta attccaatct ttcttgccct ttagctttga tagatttgaa atcttctcct    31500
tcaacataac cactatcttc aagatatttt tttaatttct cataagatga gtgggacgta    31560
ctaattcggt gtgctgtatg aagaatgctt aagccttgtt caagtgacca taattcaagg    31620
atatatacaa tttctgtttt accattccgc cgtgggattg aatatccaaa cttttggtgt    31680
gtccataacc catcttcatc aatggccata acctctttca aaaggttctt ttgccatgga    31740
taacactcat gtttagattt ttcgtatatc tcaatagctt cttgatattt tgtttcagta    31800
aatggaagta ttaccgattg agtaggatac tgattgccaa atctttttc agcagtcatg    31860
ttactcctcc ttcaatctaa atgcatgata accctatcgc tgggatgagt tattttttac    31920
tttttagatt caaattttta cgttcagcaa tctttgcttc tttatctggg tcaacccagt    31980
ttttagacca aacatcttga cgcttttat caatatctct agggtcgtat tctactgtgc    32040
aacggcaacg ctcatggcga tgatacacat cgcttggaac attaggataa tcgtatgaac    32100
ctgccaaatt tctacaccaa tcgcatgctt tacctactaa ctttcttaca attttgggtt    32160
ttaaacctgc ttttgcttga aaatcaatat ttttcttaag cgtatcatca acaacactct    32220
ggctaaatgt tactattggc tctttcaaaa gccaaagtat tttttcaaaa tcatcttcac    32280
tagaaatacg gttaacaatg ccatcaattc tatcttggtt taattctggt acttgtgatt    32340
ttaatttaaa tccagctaat tgattaagtt cactttgaac atccgttgaa taccctgaaa    32400
ttaaatcaaa attttcttc aatatggaat tgaacaatct atctgcaatg ttgaaataca    32460
ttttccgtc aggtaaaaca tctactgtta cgtgagttcc caaaacatca gataaaattt    32520
gaccaacttc aataccaaat tcattgctt gaatataagt tgctttttta gttttcaaca    32580
attccaatga ttgctttaac ttttactat ttgctgctct ttcatcaaaa tcttgattaa    32640
ttttttctaa aagagatggt aaaatgtctt ccattattca gctcctttaa ttccagttaa    32700
atcacgaata gtatctttat tgatgaactc aggaattgct tgattaagtt taatagcacc    32760
atctccaatt aaacttaaca tgcttgcatc agcttcaaac aatggttccc atttcggttt    32820
```

```
tgttttgcta aactgttctc ttagataagg tacatcatca cgcaaacatg ctgcaagata  32880
agctacattt agtaatcctg ctcccaaact tcgttgagcc tttctaccag ccaatcttaa  32940
attttcatga cttgccttaa ttgcttcaac cgatgatgga ttatcagaaa tgaatcctaa  33000
atcatcaaga gttaatccag tttcaccagc aaaaccagcc gctgcagttc tgagttgttc  33060
agtaaatggc gacatgcttg gttgagtaaa ttgtccaaga gttggtttat cgccatcctc  33120
gtcttttgta aattgcaaca tgcttgaaac tgttgctttc caagtttcca ttggctccgc  33180
atcatcactc aatccagtta catattttg agggaaagaa taaaactcag cagttacatc  33240
agctctttca agtgttcgtt ttgcattgct ttgccaatac attcctgaac gtgtaatacg  33300
agaacgacca aaaggacgaa ctgcatcagg acggtgaatg ataggcacta acagtggatg  33360
acctgttgga tttgcaatcg aaatattatt acgtgaatca cgataataat aatctgttct  33420
atcaggcaag aaatgagctt caagaacaac attattgttt tcatctcgtt ctaaaactgc  33480
atatccctct gtcagtaatc cagtaattgg gtcaatgatt cctgttgcat tgatagcttc  33540
aataacttga agtcgtactg catcattttc acctttagaa atataagtaa agctacatga  33600
tgcaataagt gatgacaaaa cagcactatc aaaaaatata tcaggattat tttcctcaaa  33660
aatttcattt actgtaaagt catcattttc aaattctcga aaacaagac ggtctgcaag  33720 actatcaact cctttgcac accaccctaa tattgaacga tattgttggc ttaatgcttg  33780
tggaattgta atccctttga atctatcaac atatttcatc gcatattgct catagcgcat  33840
ttctgctctt cgtttatgaa cagatagctt aaatctcagg tatccaatac ctttttcagt  33900 caatttttg ctcctttctc tcgtctttaa gatattgaac aattctcata tatctttccc  33960
gactaaaaac attactattt ttataccaaa caaaaaagtc atcattcctt ttactagaat  34020
tacaacttct acaagccgga actacatttc cataagaata tgcgccacca tcaattaatg  34080
ggacgacatg ttcatgatgt aaatgctcgc cataaatttc tagagacttt ttttcaggca  34140
taccacagta agcacagctg caacaaaaaa atgacttaat ttcaagccat tcttttctg  34200 tcaaggtact ttcagagcca tatttcaaag ttctagactt tgcacaagtc attcgtcgtc  34260
ttgtaggatt atttttacac caatcttttt ctgactgacg acacttacct ttatttcgt  34320 tgtaataacc taattgccgt tctttgattt tatctgcatt ttttcataa tatctctttt  34380 tctgctctaa aatctttct tttttcgcct catatcttgc tttatcttta gcttttcggc  34440
agactttaca tcgcccttca aatccaccttt ttctcttaaa attttagga aaattatgtt  34500 catctagctc tttttcttgc ttacagatgc tacaaattct tttcattatt atctcctttt  34560
tctcgctcaa gaaaaaatat gtacagt                                       34587
```